Figure 1:
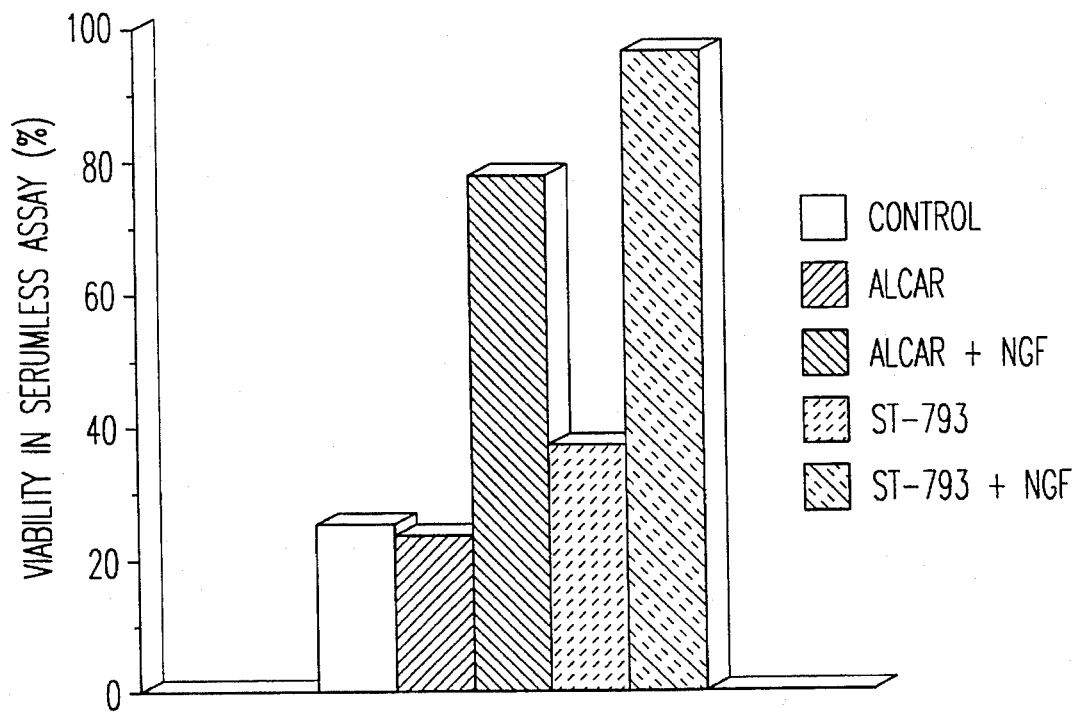

United States Patent [19]

Tinti et al.

[11] Patent Number: 5,534,549
[45] Date of Patent: * Jul. 9, 1996

[54] EASTERS OF ACYL L-CARNITINES WITH GAMMA-HYDROXYBUTYRIC ACID AND PHARMACEUTICAL COMPOSITIONS CONTAINING THEM FOR INHIBITING NEURONAL DEGENERATION AND FOR THE TREATMENT OF COMA

[75] Inventors: Maria O. Tinti; Domenico Misiti; Claudio Cavazza, all of Rome; Nazareno Scafetta, Pavona, all of Italy

[73] Assignee: Sigma-Tau Industrie Farmaceutiche Riunite S.p.A., Rome, Italy

[*] Notice: The portion of the term of this patent subsequent to Oct. 4, 2014, has been disclaimed.

[21] Appl. No.: 395,914

[22] Filed: Feb. 28, 1995

Related U.S. Application Data

[63] Continuation of Ser. No. 317,750, Oct. 4, 1994, abandoned, which is a continuation of Ser. No. 984,736, Dec. 2, 1992, abandoned, which is a continuation of Ser. No. 649,046, Feb. 1, 1991, abandoned.

[30] Foreign Application Priority Data

Feb. 12, 1990 [IT] Italy ........................ 47618/90

[51] Int. Cl.⁶ .................................................. A16K 31/22
[52] U.S. Cl. ............................. 514/551; 560/170
[58] Field of Search ..................... 560/170; 514/547, 514/551

[56] References Cited

U.S. PATENT DOCUMENTS 4,439,438  3/1984  Cavazza ..................... 560/170
5,412,113  5/1995  Giannessi ..................... 549/328

OTHER PUBLICATIONS

"Hackh's Chemical Dictionary,"4ᵗʰEd., pp. 16, 85 & 86 (1972).
"Cecil Textbook of Medicine,"19ᵗʰ Ed., 2, pp. 2075–2079 2013–2133 (1993).

Primary Examiner—Michael L. Shippen
Attorney, Agent, or Firm—Oblon, Spivak, McClelland, Maier & Neustadt

[57] ABSTRACT

The esters of acyl L-carnitines with gamma-hydroxybutyric acid in the form of pharmacologically acceptable salts of formula (I)

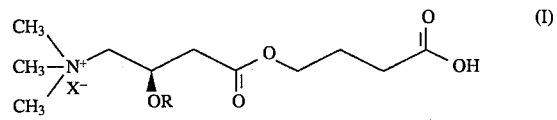

wherein X⁻ is the anion of a pharmacologically acceptable salt, e.g. chloride, bromide, orotate, acid aspartate, acid citrate, acid phosphate, acid fumarate, lactate, acid maleate, acid oxalate, acid sulfate and glucosephosphate or in the form of inner salts of formula (I')

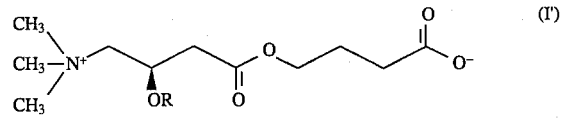

wherein R is a straight or branched acyl group having from 2 to 5 carbon atoms, such as e.g. acetyl, propionyl, n,butyryl, isobutyryl and isovaleryl, are active in inhibiting neuronal degeneration (as it occurs in Alzheimer's senile dementia and Parkinson's disease) and in the treatment of coma.

32 Claims, 1 Drawing Sheet

EASTERS OF ACYL L-CARNITINES WITH GAMMA-HYDROXYBUTYRIC ACID AND PHARMACEUTICAL COMPOSITIONS CONTAINING THEM FOR INHIBITING NEURONAL DEGENERATION AND FOR THE TREATMENT OF COMA

This is a continuation of application Ser. No. 07/317,750, filed on Oct. 4, 1994, abandoned, which is a continuation of application Ser. No. 07/984,736, filed on Dec. 2, 1992, abandoned, which is a continuation of application Ser. No. 07/649,046, filed on Feb. 1, 1991, abandoned.

The present invention relates to the esters of acyl L-carnitines with gamma-hydroxybutyric acid in the form of their pharmacologically acceptable salts of formula (I)

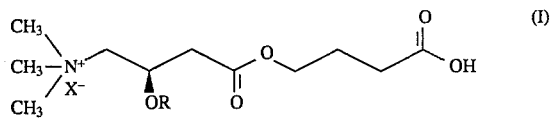

wherein $X^-$ is the anion of a pharmacologically acceptable acid e.g. chloride, bromide, orotate, acid aspartate, acid citrate, acid phosphate, acid fumarate, lactate, acid maleate, acid oxalate, acid sulfate and glucosephosphate, or in the form of inner salts of formula (I')

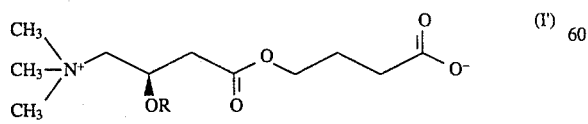

wherein R is a straight or branched acyl group having from 2 to 5 carbon atoms, such as for instance acetyl, propionyl, n-butyryl, isobutyril and isovaleryl.

These compounds are active in inhibiting neuronal degeneration (as it occurs in Alzheimer's senile dementia and Parkinson's disease) and in the treatment of coma.

The present invention also relates to orally or parenterally administrable pharmaceutical compositions for treating the foregoing pathologies, which comprise one of the compounds of formula (I) or (I') as active principle.

Esters of carnitine with hydroxy-substituted saturated organic acids (e.g. 2-hydroxybutyric, 2-hydroxy-2-methylbutyric and 2-methyl-3-hydroxy propionic acid) are known already; see e.g. U.S. Pat. No. 4,766,222 assigned to Sigma-Tau Industrie Farmaceutiche Riunite S.p.A. These compounds, however, are O-esters (i.e. esters on the carnitine hydroxyl group) and endowed with pharmacological properties entirely different from and in no way related to the properties of the esters of the present invention.

Esters on the carnitine carboxyl group are described in Z. Physiol. Chem., 295, 377, 1953 e Z. Physiol. Chem., 346, 314, 1966. These are, however, esters of carnitine with aliphatic alcohols, such as methanol, ethanol and butanol, or with aromatic alcohols such as benzyl alcohol, not with hydroxy-acids.

The examples that follow show the preparation of the esters of acyl L-carnitine with gamma-hydroxybutyric acid via the synthesis scheme which is illustrated hereinbelow.

Synthesis scheme of the esters of acyl L-carnitines with gamma-hydroxybutyric acid

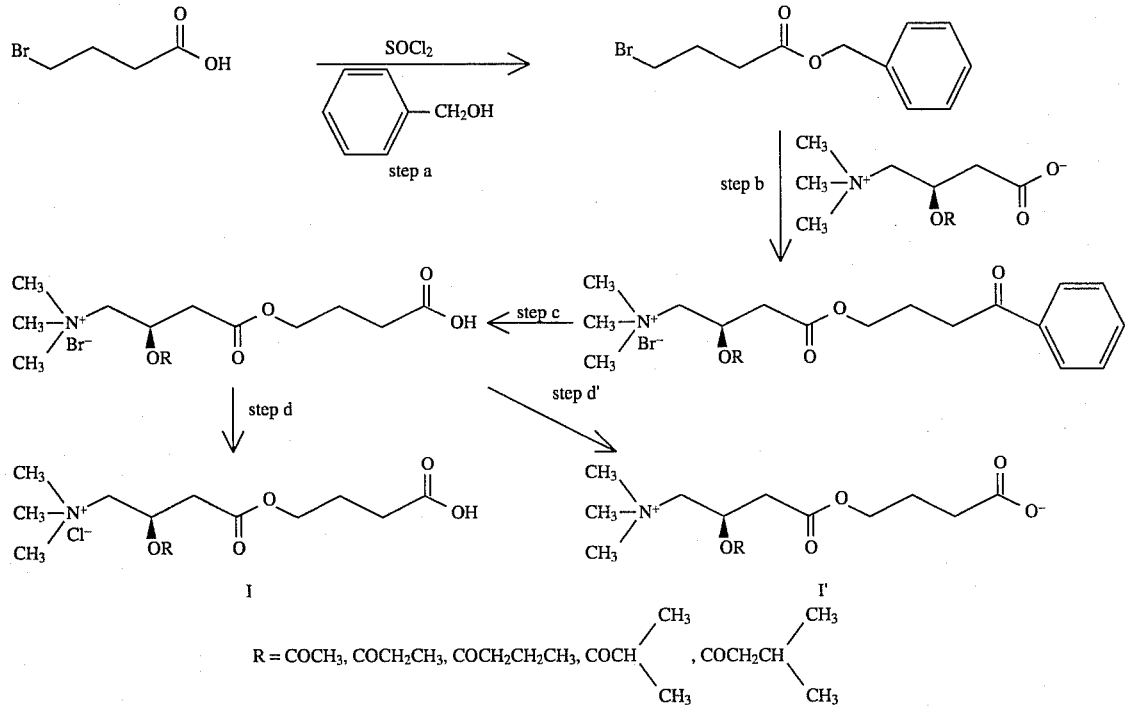

EXAMPLE 1

Preparation of the Ester of Acetyl L-Carnitine with Gamma-Hydroxybutyric Acid (ST 793)

Step a: Preparation of the benzyl ester of gamma-bromobutyric acid

Gamma-bromobutyric acid (3.3 g; 0.02 moles) was suspended in benzyl alcohol (15 ml). The suspension was cooled to 0° C. and thionyl chloride (8 ml; 0.01 moles) was slowly added dropwise thereto. The reaction mixture was kept at room temperature for 16 hours and then concentrated under vacuum to remove thionyl chloride and distilled to remove benzyl alcohol. The distillation residue was purified via chromatography on silica gel, with hexane-AcOEt (98:2) as eluant.

TLC hexane; $R_F=0.2$

NMR CDCl$_3$ δ 7.2 (5H,s,aromatic); 5,0(2H,s,CH$_2$-benzyl) 3.3

(2H,t,CH$_2$COO); 2.6–2.0(4H,m BrCH$_2$CH$_2$)

Step b: Preparation of the ester of acetyl L-carnitine with benzyl gamma-bromobutyrate Acetyl L-carnitine inner salt (1.62 g; 0.008 moles) was suspended in 12 ml anhydrous dimethyl formamide. To the suspension, gamma-bromobutyric acid benzyl ester (2.05 g; 0.008 moles) was added.

The reaction mixture was kept under stirring at room temperature for 24 hours in a nitrogen atmosphere. Ethyl ether was then added until complete precipitation of the reaction product. The product was isolated by filtration. 3.43 g of the title product were obtained.

TLC CHCl$_3$ 4.2—H$_2$O 1.1—Isopr OH 0.7—CH$_3$COOH 1.1

MetOH 2.8; $R_F=0.8$

HPLC column μBondapack C18

Eluant KH$_2$PO$_4$ 0.005M—CH$_3$CN: 70–30 flow rate 1 ml/min $R_t$: 12.9

NMR D$_2$O δ 7.4(5H, s, aromatic);
5.6(1H, m, CH) 5.2(2H, s, CH$_2$-benzyl); 4.4–4.0
|
OCO (4H,m,N$^+$CH$_2$,OCH$_2$); 3.5 (9H,s,(CH$_3$)$_3$N$^+$); 3.2(2H,d, CH—CH$_2$COO);

2.3(2H,m,CH$_2$CH$_2$COO); 2.0(5H,m$^+$,CH$_2$CH$_2$CH$_2$; COCH$_3$)

Step c: Preparation of the ester of acetyl L-carnitine bromide with gamma-hydroxybutyric acid The product of step b (1 g) was dissolved in 20 ml absolute ethanol. The resulting solution was hydrogenated in the presence of 100 mg 10% Pd/C under 3 atmospheres of hydrogen for 30 minutes. The mixture was filtered and concentrated under vacuum. 0.75 g of the title product were obtained.

Yield 98%

TLC as in step b; $R_F=0.7$

Step d: Preparation of the ester of acetyl L-carnitine with gamma-hydroxybutyric acid inner salt (I').

The product of step c (1 g) was eluted through 30 ml strongly basic resin (AMBERLITE IRA 402) activated in the HCO$_3^-$ form. The eluate was lyophilized. An extremely hygroscopic solid product was obtained.

NMR(D$_2$O): δ 5.6(1H, m, CH);
|
OCO 4.2(2H, t, —CH$_2$O); 3.7(2H, d, —N$^+$CH$_2$—);

3.2(9H,s,(CH$_3$)$_3$N$^+$); 2.8(2H,d,CH$_2$COO); 2.3–2.0(5H, m+s,

CH$_2$COOH; COCH$_3$); 1.8(2H,m,CH$_2$—CH$_2$COOH)

$[\alpha]_D^{25} = -18.0$ (C = 1, H$_2$O)

HPLC

Column spherisorb—SCX 5M

Eluant KH$_2$PO$_4$ 0.005M—CH$_3$CN (35–65); pH=4.2

Flow rate 1 ml/min

Detector UV 205 nm

Rt=8.83

TLC as in step b; $R_F=0.5$

EXAMPLE 2

Preparation of the Ester of Isovaleryl L-Carnitine with Gamma-Hydroxybutyric Acid (ST 794).

Step a: as in Example 1

Step b: Preparation of the ester of isovaleryl L-carnitine with gamma-hydroxybutyric acid benzyl ester.

Isovaleryl L-carnitine inner salt (2 g;. 0.01 moles) was suspended in 15 ml dimethyl formamide and to the resulting mixture 4-bromo butyric acid benzyl ester (2.65 g; 0.01 moles) was added. The reaction mixture was kept under stirring at room temperature in a nitrogen atmosphere overnight. Ethyl ether was then added to the mixture until complete precipitation. 2 g of the compound were obtained.

TLC as in step b of example 1: $R_F=0.7$

HPLC

Column μBondapack C$_{18}$

Eluant KH$_2$PO$_4$: 0.05M—CH$_3$CN, 50—50

Flow rate 1 ml/min $R_f$=9.272

NMR D$_2$O δ 7.2(5H, s, aromatic);
5.6(1H, m, CH); 5.0(2H, s, CH$_2$—Ar); 4.0
|
OCO (2H,t,COOCH$_2$); 3.9–3.6 (2H,m,N$^+$CH$_2$); 3.2(9H,s, (CH$_3$)$_3$N$^+$ )2.8(2H,m,CHCH$_2$ COO); 2.4(2H, t, CH$_2$CH$_2$COO); 2.2(2H, d, OCOCH$_2$);
                           CH$_3$
                          /
2.0–1.8(3H, m, CH
                          \
                           CH$_3$ CH$_3$
                                   /
CH$_2$CH$_2$CH$_2$COO); 0.9(6H, d, CH         )
                                   \
                                    CH$_3$ Step c: Preparation of the ester of isovaleryl L-carnitine bromide with gamma-hydroxybutyric acid.

The product of step b (1 g) was dissolved in 20 cc H$_2$O and hydrogenated in the presence of 10% Pd/C at a pressure of 3 atmospheres for 30 minutes. The mixture was filtered and concentrated under vacuum. 0.78 g were obtained.

Yield 98%

HPLC

Column spherisorb-SCX

Eluant CH$_3$CN—KH$_2$PO$_4$ 0.5M: 65–35

Flow rate 1 ml/min
R$_f$=6.46

NMRD$_2$O δ 5.7(1H, m, CH); 4.2(2H, t, —COOCH$_2$);
   |
   OCO
4.0–3.7(2H, m, N$^+$CH$_2$);

3.2(9H,s,(CH$_3$)$_3$N$^+$); 2.9(2H,d,CH<u>CH$_2$</u>—COO); 2.4(4H,m, OCOCH$_2$+

<u>CH$_2$</u>COOH); 2.0(3H, m, 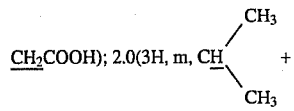

<u>CH$_2$CH$_2$</u>CH$_2$); 0.9(6H, d, 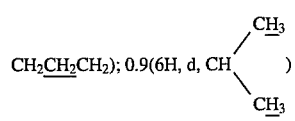

[α]$_D^{25}$=−15.1 (C=1% H$_2$O)

EXAMPLE 3

Preparation of the Ester of Isobutyryl L-Carnitine Chloride with Gamma-Hydroxybutyric Acid (ST 878).

Step a: same as in Example 1.
Step b: preparation of the ester of isobutyryl L-carnitine bromide with gamma-hydroxybutyric acid benzyl ester.

This step was carried out as step b in Example 1, except that isobutyryl L-carnitine inner salt was substituted for acetyl L-carnitine inner salt

[2]=−11.7(C=1% H$_2$O)
HPLC
column μBondapak C$_{18}$ 3.9 mm ID
mobile phase KH$_2$PO$_4$ 0.05M —CH$_3$CN (70–30)
flow rate 1.4 ml/min
Rt=20.54 min NMRD$_2$O δ 7.3(5H, s, benzyl);
5.6(1H, m, CH); 5.1(2H, s, CH$_2$-benzyl); 4.2–3.8
   |
   OCO (4H,m,COO<u>CH$_2$</u>CH$_2$;NCH$_2$—); 3.2 (9H,s,(CH$_3$)$_3$N); 2.8 (2H, CH—<u>CH$_2$</u>COO); 2.5–2.2 (3H,m,CH$_2$ <u>CH$_2$</u>COOH,OCOCH); 1.8 (2H,q,<u>CH$_2$</u>CH$_2$COO);

1.1(6H, d, 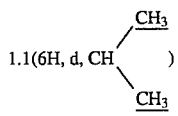

Yield: 95%
Step c: preparation of the ester of isobutyryl L-carnitine chloride with gamma-Hydroxybutyric acid.

The product of step b was hydrogenated as described in step c of Example 1. The product thus obtained was converted directly into chloride with AMBERLITE IRA 402 resin activated in Cl$^-$ form. The eluate was lyophilized thus giving the title product.

[2]=−29.7 (C=1% H$_2$O)
HPLC
column μBondapak NH$_2$ 10μ
mobile phase KH$_2$PO$_4$ 0.05M —CH$_3$CN (35–65)
flow rate 1 ml/min
Rt=5.26 min NMRD$_2$O δ 5.6(1H, m, CH); 4.2(2H, t, COOCH$_2$);
   |
   OCO
3.8(2H, m, NCH$_2$)3.2

(9H, s, (CH$_3$)$_3$N$^+$); 2.9(2H, d, CH—<u>CH$_2$</u>COO);

2.7–2.2(3H, m, OCOCH 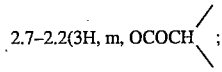 ;

<u>CH$_2$</u>COOH); 1.8 (2H,q,<u>CH$_2$</u>CH$_2$COOH);

1.0(6H, d, 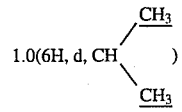

TLC silica gel:
CHCl$_3$-4-IsoprOH 0.7-MetOH-3—CH$_3$COOH—1-H$_2$O 1;
Rf=0.65.

|  | E.A. C$_{15}$H$_{28}$ClNO$_6$ | | | | |
|---|---|---|---|---|---|
|  | C % | H % | N % | Cl % | KF 2% |
| calc. | 50.91 | 7.97 | 3.95 | 10.02 |  |
| calc. with 2% H$_2$O | 49.89 | 8.04 | 3.87 | 9.81 |  |
| found | 50.00 | 8.43 | 4.07 | 9.98 |  |
| Yield: 98% | | | | | |

EXAMPLE 4

Preparation of the Ester of Propionyl L-Carnitine Chloride with Gamma-Hydroxybutyric Acid (ST 880).

Step a: as in Example 1.
Step b: preparation of the ester of propionyl L-carnitine bromide with gamma-hydroxybutyric acid benzyl ester.

This step was carried out as step b in Example 1, except that propionyl L-carnitine inner salt was substituted for acetyl L-carnitine inner salt.

[2]=−12.8(C=1% H$_2$O)
HPLC
Column μBondapak C$_{18}$ 3.9 mm ID
mobile phase NaClO$_4$ 0.05M—CH$_3$CN (70–30)
flow rate 2 ml/min
Rt=20.9 min NMRD$_2$O δ 7.4(5H, s, benzyl);
5.8(1H, m, CH); 5.1(2H, s, CH$_2$-benzyl); 4.2
   |
   OCO (2H,t,O—<u>CH$_2$</u>CH$_2$); 3.8(2 H,m,N$^+$—CH$_2$); 3.3 (9H,s, (CH$_3$)$_3$N$^+$);2.8(2H,d,CH—<u>CH$_2$</u>COO); 2.6–2.3 (4H,m, <u>CH$_2$</u>CH$_3$; CH$_2$—<u>CH$_2$</u>—COO); 2.0 (2H,q,CH$_2$—<u>CH</u> $_2$CH$_2$);

1.1(3H,t,CH$_2$—C̲H̲$_3$)

Yield: 70%

Step c: preparation of the ester of propionyl L-carnitine chloride with gamma-hydroxybutyric acid.

The product of step b was hydrogenated as described in step c of Example 1. The product thus obtained was converted directly into chloride using an AMBERLITE IRA 402 resin activated in Cl$^-$ form. The eluate was lyophilized thus giving the title product.

[2]=−22.2 (C=1% H$_2$O)

HPLC column μBondapak—NH$_2$ (10μ)

mobile phase KH$_2$PO$_4$ 0.05M—CH$_3$CN (35–65)

flow rate 1 ml/min

Rt=6.16 min

NMRD$_2$O δ 5.7(1H, m, C̲H̲); 4.2(2H, t, COOC̲H̲$_2$);
$$\underset{3.9-3.7(2H,\ m,\ NCH_2)}{\overset{|}{OCO}}$$

3.2(9H,s,(CH$_3$)$_3$N$^+$); 2.8(2H,d,CH C̲H̲$_2$COO);2.7–2.3(4H,m,C̲H̲$_2$CH$_3$;COOC̲H̲$_2$ CH$_2$);2.0(2H, m,C̲H̲$_2$CH$_2$COOH); 1.1(3H,t.CH$_2$C̲H̲$_3$)

TLC silica gel

CHCl$_3$—4-Isopr OH-0.7-MetOH-3—CH$_3$COOH—1-H$_2$O 1

Rf=0.55

Yield: 98%

Pharmacological Studies

Several pharmacological studies were conducted on the compounds of the present invention. The results of some studies relating to the enhancement of the action of nerve growth factor (NGF) on PC 12 cells brought about by acetyl L-carnitine gamma-hydroxybutyrate (ST 793) are hereinbelow illustrated.

One event that is common to the physiology and pathophysiology of the aging process in the central nervous system (CNS), is the reduction of the nerve growth factor (NGF) receptors. NGF is a polypeptide that is essential for the development and maintenance of some neurons of the peripheral nervous system (PNS), where it plays a key role in the regulation of neuronal cell death. The NGF produced by target tissues binds to specific receptors (NGFR) at growth cones and is transported retrogradely to the neuronal cell body. The resulting continuous supply of target-derived NGF is essential for the preservation of the innervating neuron. In the CNS, NGF also has trophic effects on the magnocellular cholinergic neurons of the basal forebrain and septum. As in the PNS, NGF is released by target tissues, such as hippocampus and frontal cortex, where it binds to NGFR on cholinergic terminals and is retrogradely transported to the cell soma in the basal forebrain and septum.

The finding that NGF exerts. neuronotrophic activity in CNS has led to the hypothesis that the reported loss of NGFR in senescence with the resulting reduction of NGF activity is responsible for neuronal cell death and shrinkage there. Consequently, the therapeutic use of NGF for the treatment of neurological diseases associated with aging has been proposed.

It is known that the treatment of rats with acetyl L-carnitine (ALCAR), a naturally occurring substance involved in mitochondrial metabolism of fatty, acids prevents certain CNS impairments in the aged. ALCAR treatment of senescent rats prevents the loss of glucocorticoid receptors in the hippocampus and improves the behavioral performances that are related to the limbic system. ALCAR padially prevents the loss of NGFR that occurs in the hippocampus and basal forebrain of aged rodents.

ALCAR has been shown to stimulate NGFR synthesis and enhance the action of NGF on PC12 cells. For the present study, the rat pheochromocytoma (PC12) cell line was chosen as an in vitro model system for NGF-responsive neurons. PC12 cells are a rat derived cell line that display NGFR similar to those described for sympathetic and sensory neurons. PC12 typically respond to NGF by elongating neurites and developing into electrically excitable cells featuring some characteristic of the post-mitotic cholinergic neuronal phenotype.

The study reported hereinbelow shows that the action of NGF on PC12 cells is enhanced by ST 793 treatment more potently than by ALCAR treatment. Thus, ST 793 is shown to prevent some degenerative processes in the aged brain by lowering the response threshold of susceptible neurons to neuronotrophic factors.

Rat pheochromocytoma (PC12) cells were grown in RPMI 1640, supplemented with 5% heat inactivated horse serum +5% heat inactivated fetal calf serum at 37° C. in a humified incubator with 5% CO$_2$ atmosphere and fed on alternate days. At subconfluency, cells were dislodged by vigorous shaking and reseeded at 1:1 ratio. Acetyl L-carnitine (ALCAR) and ST 793 were dissolved in RPMI and added to cells at the final concentrations indicated in the various experiments.

Neurite outgrowth experiment

PC12 cells were plated out into 35 mm Petri dishes at a density of 2×10$^5$ cells/ml. On the sixth day of either ALCAR or ST 793 treatment (1 mM), the cells were added with NGF dissolved in RPMI 1640 at a final concentration of 100 mg/ml (3.7 nM). On day 5 after NGF addition, 100–120 cells from 5–12 randomly chosen microscope fields were counted and assayed for presence of neurites. All the counts were done independently by two investigators on coded samples. After all counts were carried out, codes were broken and the average of the two counts taken as final value estimation. The results were as follows:

| Effects of ST-793 on PC-12 | | |
|---|---|---|
| Compound | Neurite Outgrowth at 6 Days | |
| Control | − | no neurites present |
| NGF | ++ | neurites present |
| ALCAR | +/− | occasional neurite outgrowth |
| ST793 | +/− | occasional neurite outgrowth |
| NGF + ALCAR | +++ | abundant neurite outgrowth |
| NGF + ST793 | ++++ | very abundant neurite outgrowth |

Serum deprivation experiments

PC12 were plated out into 24-well plates at a density of 5×10$^4$ cells/ml and treated for 6 days with either ALCAR or ST 793 at 1 mM. After 6 days, the serum was removed from the culture medium and the cells were given NGF at 1 mg/ml (3.7 pM). After 48 hours the medium was removed, replaced with fresh medium containing 2 μCi/ml of $^{35}$S-methionine and cells were then incubated for 4 hours at 37° C. as described elsewhere. After incubation, cells were washed in PBS, solubilized with 0.5 N NaOH and the protein precipitated by addition of 50% trichloroacetic acid (TCA). Prior to TCA precipitation, aliquots from each sample were taken for protein assay. Samples were then passed through GF/F Whatman filters and washed with 5 vols. of 5% TCA. Filters were transferred into scintillation vials and, after addition of 5 ml of scintillation cocktail (Beckman), counted for radioactivity in a β-counter. The results, expressed as percent of cells surviving the serum deprivation, are shown in FIG. 1. Effect of ALCAR and ST-793 on choline acetyltransferase (ChAT).

The method described by Fonnum, F. in "A rapid radiochemical method for the determination of choline acetyltransferase", J. of Neurochem. (1975) vol. 24, 407:409 was used. Briefly, the compounds were added to the culture medium at final concentration of 1 mM.

The cells were grown for 6 days in the presence of ST 793. The medium was changed every other day.

Figure 2:
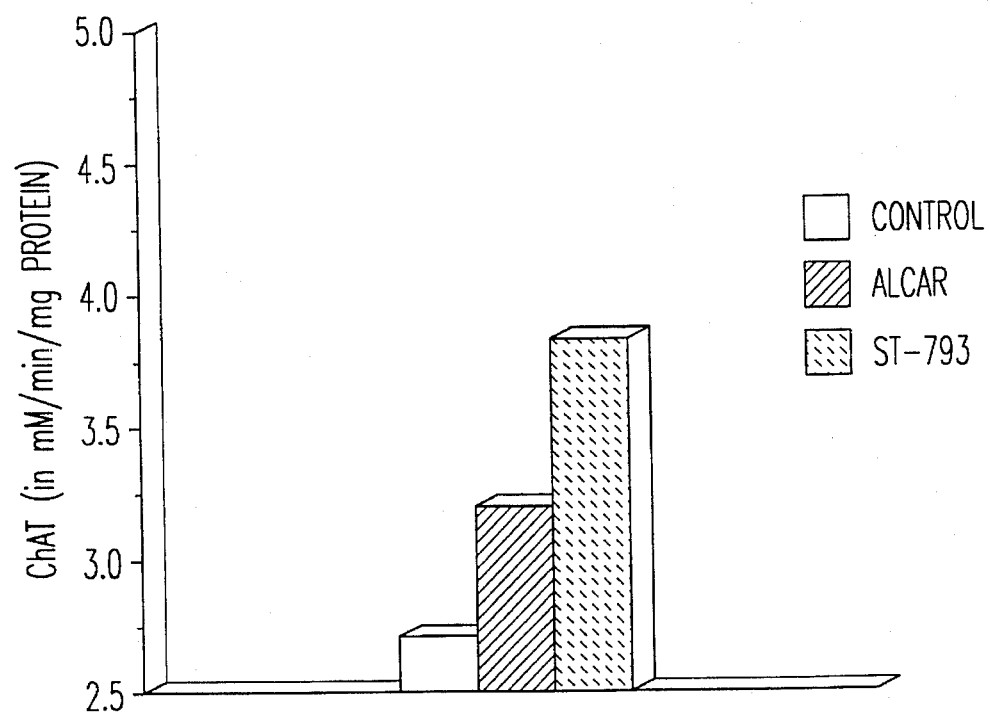

On the sixth day the cells were harvested and resuspended directly in a homogenization buffer for ChAT activity assay. Protein content was assayed on an aliquot of the cell suspensions. The results are shown in FIG. 2.

The compounds of the present invention are orally or parenterally administered, in any of the usual pharmaceutical forms which are prepared by conventional procedures well-known to those persons skilled in pharmaceutical technology. These forms include solid and liquid oral unit dosage forms such as tablets, capsules, solutions, syrups and the like as well as injectable forms, such as sterile solutions for ampoules and phials.

For these pharmaceutical forms the usual solvents, diluents and excipients are used. Optionally, sweetening, flavouring and preservative agents can also be present. Non limiting examples of such agents are sodium carboxymethylcellulose, polysorbate, mannitol, sorbitol, starch, avicel, talcum and other agents which will be apparent to those skilled in the pharmaceutical technology.

The dose which is administered will be determined by the attending physician having regard to the age, weight and general conditions of the patient, utilizing sound professional judgement. Although effective results can be noticed at doses as low as 5 to 8 mg/kg of body weight daily, a dose of from about 10 to about 50 mg/kg of body weight is preferred. Whenever necessary, larger doses can be safely administered in view of the low toxicity of the compounds of this invention.

As non-limiting examples and depending on the specific pharmaceutical form of administration, the following dosages can be indicated:

| | |
|---|---|
| for the phials: | from 5 to 500 mg |
| for the capsules: | from 15 to 50 mg |
| for the tablets: | from 15 to 500 mg |
| for the oral solutions: | from 15 to 50 mg |

We claim:

1. A compound of formula (I):

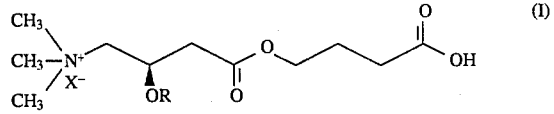

wherein $X^-$ is an anion of a pharmacologically acceptable acid and R is a straight or branched alkanoyl group having from 2 to 5 carbon atoms.

2. The compound of claim 1, wherein R is acetyl.
3. The compound of claim 1, wherein R is propionyl.
4. The compound of claim 1, wherein R is n-butyryl.
5. The compound of claim 1, wherein R is isobutyryl.
6. The compound of claim 1, wherein R is isovaleryl.
7. The compound of claim 1, wherein $X^{31}$ is selected from the group consisting of chloride, bromide, orotate, acid aspartate, acid citrate, acid phosphate, acid fumarate, lactate, acid maleate, acid oxalate, acid sulfate, and glucosephosphate.

8. A compound of formula (I'):

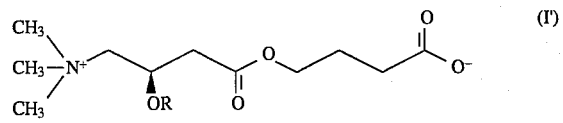

wherein R is a straight or branched alkanoyl group having from 2 to 5 carbon atoms.

9. The compound of claim 8, wherein R is acetyl.
10. The compound of claim 8, wherein R is propionyl.
11. The compound of claim 8, wherein R is n-butyryl.
12. The compound of claim 8, wherein R is isobutyryl.
13. The compound of claim 8, wherein R is isovaleryl.
14. A composition, comprising:
(a) a compound of formula (I):

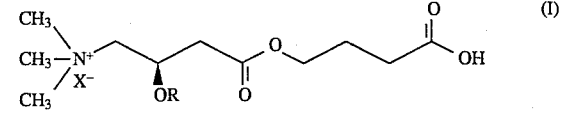

wherein $X^-$ is an anion of a pharmacologically acceptable acid and R is a straight or branched alkanoyl group having from 2 to 5 carbon atoms; and (b) a pharmaceutically acceptable excipient.
15. The composition of claim 14, wherein R is acetyl.
16. The composition of claim 14, wherein R is propionyl.
17. The composition of claim 14, wherein R is n-butyryl.
18. The composition of claim 14, wherein R is isobutyryl.
19. The composition of claim 14, wherein R is isovaleryl.
20. The composition of claim 14, wherein $X^-$ is selected from the group consisting of chloride, bromide, orotate, acid aspartate, acid citrate, acid phosphate, acid fumarate, lactate, acid maleate, acid oxalate, acid sulfate, and glucosephosphate.
21. The composition of claim 14, wherein said compound of formula (I) is present in an amount between about 5 and about 500 mg per unit dosage.
22. The composition of claim 14, wherein said compound of formula (I) is present in an amount effective for inhibiting neuronal degeneration.
23. The composition of claim 14, wherein said compound of formula (I) is present in an amount effective for treating coma.
24. A composition, comprising:
(a) a compound of formula (I'):

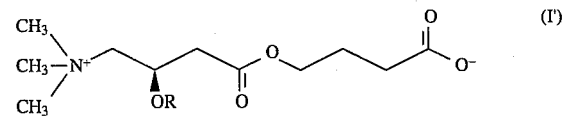

wherein R is a straight or branched alkanoyl group having from 2 to 5 carbon atoms; and (b) a pharmaceutically acceptable excipient.
25. The composition of claim 24, wherein R is acetyl.
26. The composition of claim 24, wherein R is propionyl.
27. The composition of claim 24, wherein R is n-butyryl.
28. The composition of claim 24, wherein R is isobutryl.
29. The composition of claim 24, wherein R is isovaleryl.
30. The composition of claim 24, wherein said compound of formula (I') is present in an amount between about 5 and about 500 mg per unit dosage.
31. The composition of claim 24, wherein said compound of formula (I') is present in an amount effective for inhibiting neuronal degeneration.
32. The composition of claim 24, wherein said compound of formula (I') is present in an amount effective for treating coma.

* * * * *

UNITED STATES PATENT AND TRADEMARK OFFICE
CERTIFICATE OF CORRECTION

PATENT NO. : 5,534,549
DATED : July 9, 1996
INVENTOR(S) : Maria O. TINTI, et al.

It is certified that error appears in the above-indentified patent and that said Letters Patent is hereby corrected as shown below:

On the title page, Items [54] and [63], the title and the Related U.S. Application Data, should read:

--[54] ESTERS OF ACYL L-CARNITINES WITH GAMMA-HYDROXYBUTYRIC ACID AND PHARMACEUTICAL COMPOSITIONS CONTAINING THEM FOR INHIBITING NEURONAL DEGENERATION AND FOR THE TREATMENT OF COMA

[63] Related U.S. Application Data

Continuation of Ser. No. 317,750, Oct. 4, 1994, Patent No. 5,543,556, which is a continuation of Ser. No. 984,736, Dec. 2, 1992, abandoned, which is a continuation of Ser. No. 649,046, Feb. 1, 1991, abandoned.--

Signed and Sealed this

Nineteenth Day of November, 1996

Attest:

BRUCE LEHMAN

Attesting Officer     Commissioner of Patents and Trademarks